United States Patent
Mitchnick et al.

(10) Patent No.: US 10,888,625 B2
(45) Date of Patent: Jan. 12, 2021

(54) DRUG DELIVERY PARTICLE FORMULATIONS WITH TARGETING MOIETIES

(71) Applicant: Particle Sciences, Inc., Bethlehem, PA (US)

(72) Inventors: Mark Mitchnick, East Hampton, NY (US); Garry Gwozdz, Nazareth, PA (US); Andrew Loxley, Philadelphia, PA (US)

(73) Assignee: PARTICLE SCIENCES, INC., Bethlehem, PA (US)

( * ) Notice: Subject to any disclaimer, the term of this patent is extended or adjusted under 35 U.S.C. 154(b) by 277 days.

(21) Appl. No.: 14/438,655

(22) PCT Filed: Oct. 29, 2013

(86) PCT No.: PCT/US2013/067241
§ 371 (c)(1),
(2) Date: Apr. 27, 2015

(87) PCT Pub. No.: WO2014/070723
PCT Pub. Date: May 8, 2014

(65) Prior Publication Data
US 2015/0297751 A1    Oct. 22, 2015

Related U.S. Application Data

(60) Provisional application No. 61/720,112, filed on Oct. 30, 2012.

(51) Int. Cl.
| | | |
|---|---|---|
| *A61K 35/00* | (2006.01) | |
| *A61K 47/68* | (2017.01) | |
| *A61K 9/16* | (2006.01) | |
| *A61K 47/69* | (2017.01) | |

(52) U.S. Cl.
CPC ........ *A61K 47/6835* (2017.08); *A61K 9/1617* (2013.01); *A61K 47/6937* (2017.08)

(58) Field of Classification Search
None
See application file for complete search history.

(56) References Cited

U.S. PATENT DOCUMENTS

| | | | |
|---|---|---|---|
| 7,534,448 B2 * | 5/2009 | Saltzman | A61K 9/0019 424/417 |
| 2009/0148384 A1 | 6/2009 | Fischer et al. | 424/9.1 |
| 2010/0196492 A1 | 8/2010 | Green et al. | 514/1.1 |
| 2011/0027172 A1 | 2/2011 | Wang et al. | 424/1.29 |

FOREIGN PATENT DOCUMENTS

| | | |
|---|---|---|
| EP | 13851283.5 | 5/2016 |
| WO | WO2005041933 | 5/2005 |
| WO | WO2008109806 | 9/2008 |
| WO | WO2009012303 A2 | 1/2009 |
| WO | WO2009012303 A9 | 1/2009 |
| WO | PCT/US2013/067241 | 5/2015 |

OTHER PUBLICATIONS

Repka et al. (Expert Opinion on Drug Delivery, 5(12) 2008). (Year: 2008).*
International Search Report in PCT/US13/67241 dated Feb. 28, 2014.

* cited by examiner

*Primary Examiner* — Meera Natarajan
(74) *Attorney, Agent, or Firm* — Licata & Tyrrell P.C.

(57) ABSTRACT

A targeted drug delivery complex containing a particle, a targeting moiety electrostatically attached to the particle, and an active pharmaceutical ingredient attached to or dispersed or dissolved within the particle is provided. Also provided are pharmaceutical formulations containing a plurality of the complexes as well as methods for use in targeting an active pharmaceutical ingredient to a selected cell or tissue and production of such formulations.

5 Claims, 1 Drawing Sheet

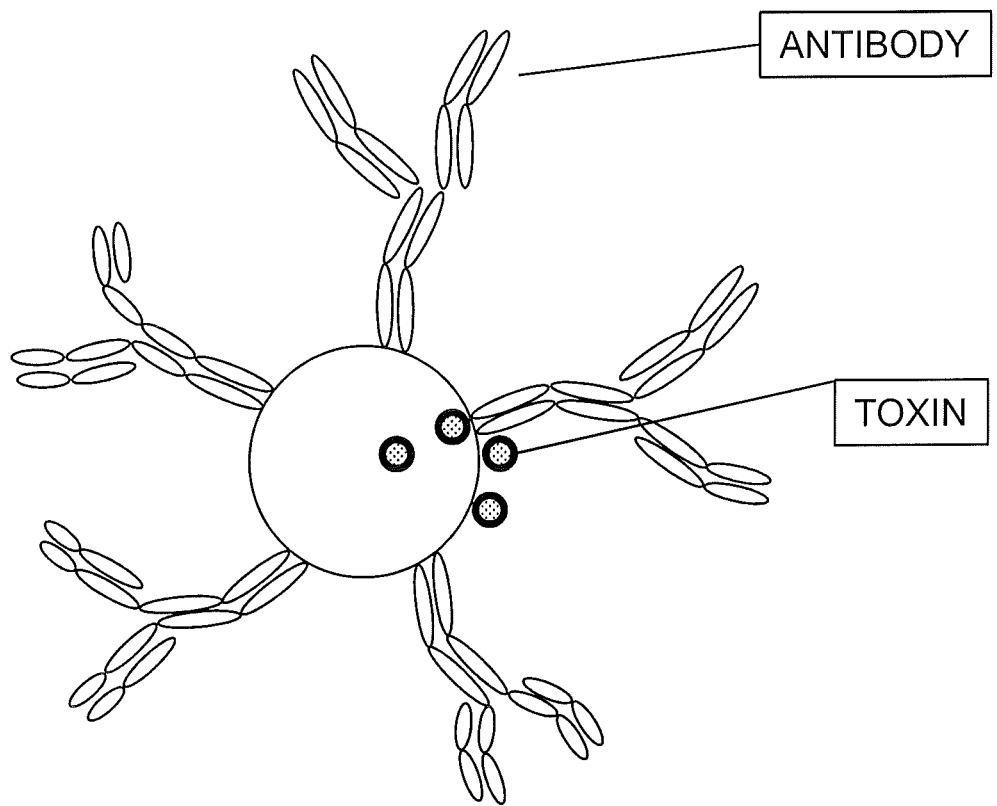

DRUG DELIVERY PARTICLE FORMULATIONS WITH TARGETING MOIETIES

This patent application is the National Stage of International Application No. PCT/US2013/067241, filed Oct. 29, 2013, which claims the benefit of priority from U.S. Provisional Application Ser. No. 61/720,112 filed Oct. 30, 2012, teachings of each of which are herein incorporated by reference in their entirety.

FIELD OF THE INVENTION

The present invention relates to a targeted drug delivery complex comprised of a particle, a targeting moiety attached to the particle and a pharmaceutically active ingredient attached to or dispersed or dissolved with the particle. The present invention further relates to particle formulations containing a plurality of these targeted drug delivery complexes. The present invention also relates to methods of targeting an active pharmaceutical ingredient to a cell or tissue via formulation of the active pharmaceutical ingredient as a targeted drug delivery complex. In one embodiment, the active pharmaceutical ingredient is a toxin.

SUMMARY OF THE INVENTION

An aspect of the present invention relates to a targeted drug delivery complex comprised of a particle, a targeting moiety attached to the particle and an active pharmaceutical ingredient attached to or dispersed or dissolved with the particle. In one embodiment, the active pharmaceutical ingredient is a toxin.

Another aspect of the present invention relates to a pharmaceutical formulation comprising a plurality of the targeted drug delivery complexes and a pharmaceutically acceptable vehicle.

Another aspect of the present invention relates to a method for targeting an active pharmaceutical ingredient to a selected cell or tissue comprising formulating the active pharmaceutical ingredient as a targeted drug delivery complex.

Another aspect of the present invention relates to a method for producing a pharmaceutical formulation targeted to a selected cell or tissue. The method comprises attaching a targeting moiety for the selected cell or tissue to a plurality of particles and further dispersing or dissolving with or attaching an active pharmaceutical ingredient to the plurality of particles.

BRIEF DESCRIPTION OF THE FIGURES

FIG. 1 is a diagram of one embodiment of a targeted drug delivery complex of the present invention. In this embodiment, the targeting moiety attached to the particle is an antibody. This embodiment further contains an active pharmaceutical ingredient, in particular a toxin, dispersed within the particle.

DETAILED DESCRIPTION OF THE INVENTION

The present invention provides targeted drug delivery complexes, pharmaceutical formulations containing of a plurality of these targeted drug delivery complexes in a pharmaceutically acceptable vehicle, methods for their use in targeting an active pharmaceutical ingredient to a selected cell or tissue and methods for production of these targeted drug delivery complexes.

Targeted drug delivery complexes of the present invention comprise a particle, an active pharmaceutical ingredient (API), and a targeting moiety.

Particles of the targeted drug delivery complexes of the present invention can be made from any number of materials or matrixes including, but in no way limited to, waxes, natural polymers, and synthetic polymers. The particles may be biodegradable such as particles constructed wholly or partially from poly (lactic-co-glycolic acid) (PLGA).

In one embodiment, lipids are used as the matrix for the particle of the targeted drug delivery complex. Examples of lipids which can be used include, but are not limited to, carnauba wax, bees wax, behenyl alcohol (docosanol), cetyl alcohol, microcrystalline triglycerides such as dynasan 118 (glyceryl tristearate) and polyethylene wax. In one embodiment, the lipid is carnauba wax including a carnauba comprising aliphatic esters, diesters of 4-hydroxycinnamic acid, ω-hydroxycarboxylic acids and fatty acid alcohols.

However, as will be understood by the skilled artisan upon reading this disclosure, particle matrices may be comprised of non-lipids as well.

In one embodiment, the matrix of the particle further comprises a surfactant. Surfactants that may be used in the particle matrices include cationic, anionic and non-ionic surfactants. Examples of such surfactants include, but are not limited to, cetyl triammonium bromide (CTAB), N-[1-(2,3-Dioleoyloxy)]-N,N,N-trimethylammonium propane methylsulfate DOTAP, cetylpyridinium bromide (CPB), polysorbate surfactants such as Tween 20, Tween 80 (polyoxyethylene sorbitan monoloaurate), polyethylene stearyl ether such as Brij 70, sodium stearate, sodium myristate, sodium dodecyl sulfate, Dioctyl sodium sulfosuccinate such as AOT and combinations thereof. The surfactant may present in a level from about 0.01% to about 10%, or from about 0.05% to about 5% or from about 0.1% to about 2% or from about 0.5% to about 2% or from about 1.0% to about 2.0%.

In one embodiment, the surface charge on the matrix is altered to optimize attachment of the targeting moiety by attaching charged moieties or adjusting the type of surfactant and/or matrix used in the production of the targeted drug delivery complex.

Particle size is preferably less than 1 μm with the particles ranging in size between about 10 nm to 1000 nm or between about 20 nm to about 900 nm or from about 30 nm to abut 800 nm or from about 40 nm to about 700 nm or from about 50 nm to about 650 nm or from about 100 nm to about 750 nm or from about 200 nm to about 750 nm or from about 300 nm to about 750 nm or from about 300 nm to about 650 nm or from about 400 nm to about 750 nm or from about 400 nm to about 660 nm or from about 500 nm to about 750 nm or from about 500 nm to about 650 nm. Particle shape may be, but is not limited to spheres, prolate and oblate spheroids, cylindrical, and irregular shapes.

The particles may be neutral or may be positively or negatively charged and may have a combination of surface charges resulting in a net neutral, positive or negative charge.

The targeted drug delivery complexes of the present invention further comprise an API. The API may be incorporated into the drug delivery particles of the present invention by one or several of the following ways. In one embodiment, the API can be solubilized in the particle resulting in a solid or liquid solution of the API in the particle material or matrix. In an alternative embodiment, the API can be dispersed within the particle material or matrix such that discrete multi-atom units of the API exist. In yet another embodiment, the API can be attached to the outside of the particle in molecular or particulate form.

Examples of APIs useful in the present invention include, but are not limited to, analgesics, anti-anginal agents, anti-asthmatics, anti-arrhythmic agents, anti-angiogenic agents, antibacterial agents, anti-benign prostate hypertrophy agents, anti-cystic fibrosis agents, anti-coagulants, anti-depressants, anti-diabetic agents, anti-epileptic agents, anti-fungal agents, anti-gout agents, anti-hypertensive agents, anti-inflammatory agents, anti-malarial agents, anti-migraine agents, anti-muscarinic agents, anti-neoplastic agents, anti-obesity agents, anti-osteoporosis agents, anti-parkinsonian agents, anti-protozoal agents, anti-thyroid agents, anti-urinary incontinence agents, anti-viral agents, anxiolytics, beta-blockers, cardiac inotropic agents, cognition enhancers, corticosteroids, COX-2 inhibitors, diuretics, erectile dysfunction improvement agents, essential fatty acids, gastrointestinal agents, histamine receptor antagonists, hormones, immunosuppressants, keratolyptics, leukotriene antagonists, lipid regulating agents, macrolides, muscle relaxants, non-essential fatty acids, nutritional agents, nutritional oils, protease inhibitors and stimulants.

In one embodiment, the active pharmaceutical ingredient is a toxin.

The targeted drug delivery complexes of the present invention further comprise a targeting moiety attached to the outside of the particle. The targeting moiety is attached to the particle electrostatically such that the attachment does not require any covalent alteration of the targeting moiety. In one embodiment, the targeting moiety binds to a selected cell or tissue. Examples of targeting moieties include, but are not limited to, antibodies, Fabs, aptamers, oligonucleotides, small molecules and carbohydrates.

The entire complex comprising the particle, API and targeting moiety is referred to herein as a targeted drug delivery complex. The targeted drug delivery complex the present invention have an average diameter of less than 100 μm, more preferably less than 10 μm, more preferably less than 1 μm.

Pharmaceutical formulations in accordance with the present invention comprise a plurality of the targeted drug delivery complexes and a pharmaceutically acceptable vehicle.

Pharmaceutically acceptable vehicles for use with the targeted drug delivery complexes of the present invention are well known in the art and taught in standard reference texts such as *Remington's Pharmaceutical Sciences*, Mack Publishing Co., Easton, Pa., 1985.

The targeted drug delivery complexes of the present invention are useful in methods of targeting an active pharmaceutical ingredient to a selected cell or tissue and producing pharmaceutical formulations targeted to a selected cell or tissue. In these methods, a targeting moiety for the selected cell or tissue is electrostatically attached to a particle. The particle further comprises the active pharmaceutical ingredient to be targeted to the cell to tissue dispersed or dissolved with or attached to the particle.

What is claimed is:

1. A targeted drug delivery complex comprising a particle, a targeting moiety attached electrostatically to the particle, and an active pharmaceutical ingredient dispersed or dissolved with or attached to the particle, wherein the targeting moiety and the active pharmaceutical ingredient are not covalently modified, wherein the particle is made of a matrix comprising cetylpyridinium bromide and a lipid, natural polymer and/or synthetic polymer, and wherein the targeting moiety is selected from an antibody or a Fab.

2. The targeted drug delivery complex of claim 1 wherein the targeting moiety binds to a selected cell or tissue.

3. The targeted drug delivery complex of claim 1 wherein the active pharmaceutical ingredient is selected from the group comprising analgesics, anti-anginal agents, anti-asthmatics, anti-arrhythmic agents, anti-angiogenic agents, anti-bacterial agents, anti-benign prostate hypertrophy agents, anti-cystic fibrosis agents, anti-coagulants, anti-depressants, anti-diabetic agents, anti-epileptic agents, anti-fungal agents, anti-gout agents, anti-hypertensive agents, anti-inflammatory agents, anti-malarial agents, anti-migraine agents, anti-muscarinic agents, anti-neoplastic agents, anti-obesity agents, anti-osteoporosis agents, anti-parkinsonian agents, anti-protozoal agents, anti-thyroid agents, anti-urinary incontinence agents, anti-viral agents, anxiolytics, beta-blockers, cardiac inotropic agents, cognition enhancers, corticosteroids, COX-2 inhibitors, diuretics, erectile dysfunction improvement agents, essential fatty acids, gastrointestinal agents, histamine receptor antagonists, hormones, immunosuppressants, keratolyptics, leukotriene antagonists, lipid regulating agents, macrolides, muscle relaxants, non-essential fatty acids, nutritional agents, nutritional oils, protease inhibitors and stimulants.

4. The targeted drug delivery complex of claim 1 wherein the active pharmaceutical ingredient is dissolved, in a liquid or solid solution, in the particle matrix and/or dispersed within the particle matrix and/or adhered to a particle surface.

5. A pharmaceutical formulation comprising a plurality of targeted drug delivery complexes of claim 1 and a pharmaceutically acceptable vehicle.

* * * * *